(12) United States Patent
Brassel

(10) Patent No.: US 8,177,790 B2
(45) Date of Patent: May 15, 2012

(54) MEDICAL RETRIEVER

(76) Inventor: Friedhelm Brassel, Duisburg (DE)

( * ) Notice: Subject to any disclaimer, the term of this patent is extended or adjusted under 35 U.S.C. 154(b) by 0 days.

(21) Appl. No.: 10/969,452

(22) Filed: Oct. 19, 2004

(65) Prior Publication Data

US 2005/0149061 A1 Jul. 7, 2005

Related U.S. Application Data

(63) Continuation of application No. PCT/EP03/04164, filed on Apr. 22, 2003.

(30) Foreign Application Priority Data

Apr. 20, 2002 (DE) .................... 102 17 757

(51) Int. Cl.
*A61F 11/00* (2006.01)
(52) U.S. Cl. ........................................ 606/108
(58) Field of Classification Search .................. 606/191, 606/108, 110, 113, 127, 128, 200, 106, 138, 606/139, 144; 623/1.11; 604/164.08, 164.12, 604/103.06, 530, 529, 532, 510
See application file for complete search history.

(56) References Cited

U.S. PATENT DOCUMENTS

| | | | | |
|---|---|---|---|---|
| 3,467,102 A | * | 9/1969 | Stark et al. | 606/194 |
| 4,738,667 A | * | 4/1988 | Galloway | 604/530 |
| 4,790,831 A | * | 12/1988 | Skribiski | 604/524 |
| 4,898,591 A | * | 2/1990 | Jang et al. | 604/527 |
| 4,925,445 A | * | 5/1990 | Sakamoto et al. | 604/528 |
| 4,950,227 A | * | 8/1990 | Savin et al. | 623/1.12 |
| 4,994,069 A | * | 2/1991 | Ritchart et al. | 606/191 |
| 5,058,595 A | * | 10/1991 | Kern | 600/468 |
| 5,112,136 A | | 5/1992 | Sakuma et al. | |
| 5,195,954 A | * | 3/1993 | Schnepp-Pesch et al. | 604/22 |
| 5,282,796 A | * | 2/1994 | Knoepfler | 606/1 |
| 5,299,574 A | * | 4/1994 | Bower | 600/435 |
| 5,357,961 A | * | 10/1994 | Fields et al. | 600/435 |
| 5,387,219 A | * | 2/1995 | Rappe | 606/108 |
| 5,445,625 A | * | 8/1995 | Voda | 604/532 |
| 5,499,991 A | * | 3/1996 | Garman et al. | 606/148 |
| 5,531,788 A | * | 7/1996 | Dibie et al. | 623/11.11 |
| 5,562,678 A | * | 10/1996 | Booker | 606/113 |
| 5,643,292 A | * | 7/1997 | Hart | 606/144 |

(Continued)

FOREIGN PATENT DOCUMENTS

DE 19514534 A1 * 10/1996

(Continued)

OTHER PUBLICATIONS

English Language Abstract of DE19514534.*

*Primary Examiner* — Gary Jackson
*Assistant Examiner* — Erin Colello
(74) *Attorney, Agent, or Firm* — David J. Aston; Peters Verny, LLP

(57) ABSTRACT

The invention relates to a device for the extraction of a spiral from a blood vessel with said device comprising a guide wire (3) which bends back on itself in its distal region where it forms into an arched structure and thus an anchoring part. The free end (7) of the guide wire (3) points towards the proximal end of said wire (3) and can be hooked onto the spiral (8) that is to be extracted.

12 Claims, 2 Drawing Sheets

U.S. PATENT DOCUMENTS

Figure 1:
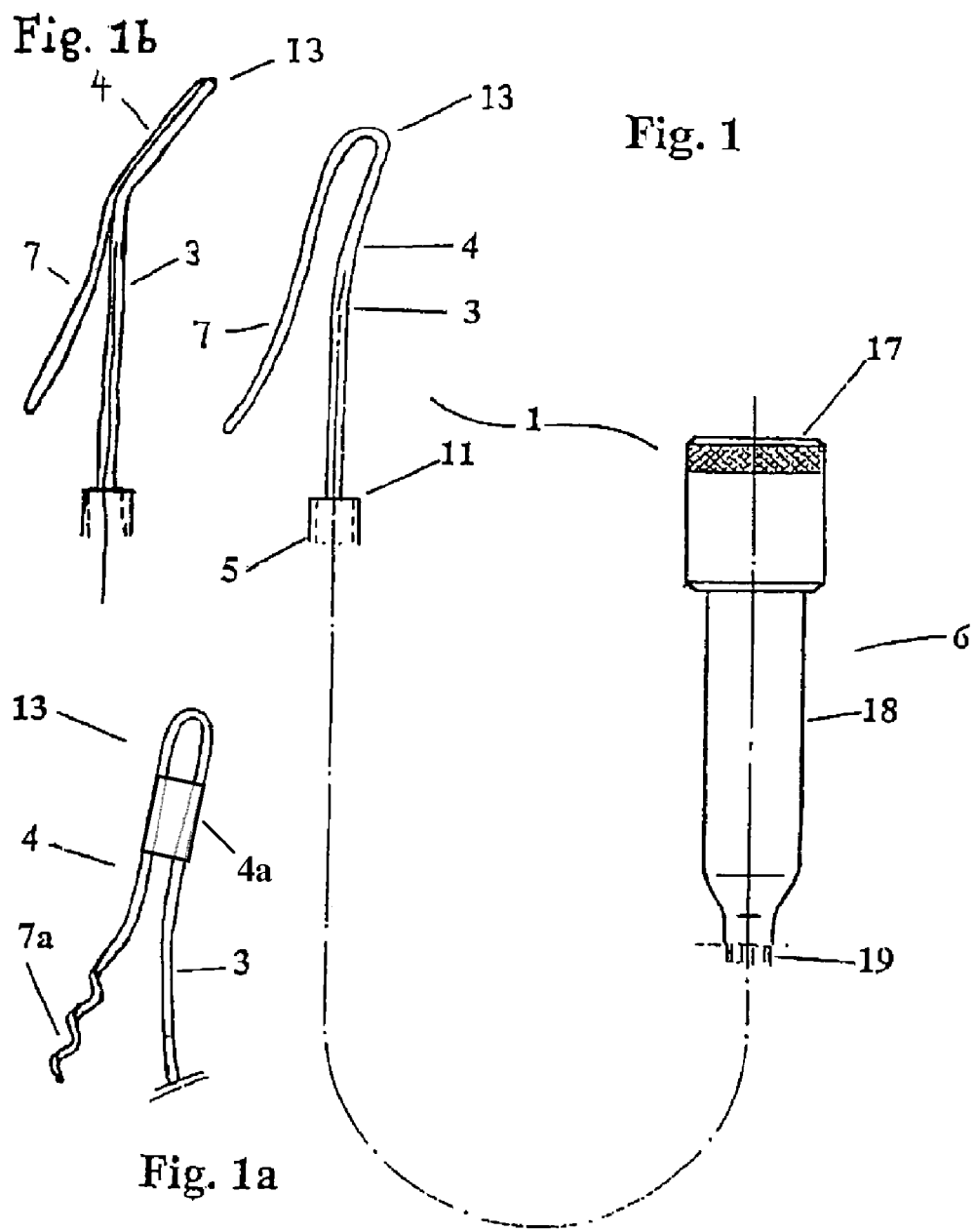

| | | | | |
|---|---|---|---|---|
| 5,658,299 A * | 8/1997 | Hart | | 606/139 |
| 5,752,961 A * | 5/1998 | Hill | | 606/113 |
| 5,782,839 A * | 7/1998 | Hart et al. | | 606/113 |
| 5,795,319 A * | 8/1998 | Ali | | 604/8 |
| 5,868,700 A * | 2/1999 | Voda | | 604/510 |
| 5,868,754 A * | 2/1999 | Levine et al. | | 606/108 |
| 6,013,086 A * | 1/2000 | Ouchi et al. | | 606/113 |
| 6,019,736 A * | 2/2000 | Avellanet et al. | | 600/585 |
| 6,210,408 B1 * | 4/2001 | Chandrasekaran et al. | | 606/41 |
| 6,251,128 B1 | 6/2001 | Knopp et al. | | |
| 6,270,495 B1 | 8/2001 | Palermo | | |
| 6,520,923 B1 * | 2/2003 | Jalisi | | 600/585 |
| 6,558,368 B1 * | 5/2003 | Voda | | 604/532 |
| 6,629,984 B1 * | 10/2003 | Chan | | 606/148 |
| 6,958,074 B2 * | 10/2005 | Russell | | 606/200 |
| 7,530,983 B1 * | 5/2009 | Jenkins | | 606/110 |
| 2002/0010426 A1 * | 1/2002 | Clayman et al. | | 604/170.01 |
| 2002/0026175 A1 * | 2/2002 | Paskar | | 604/528 |

FOREIGN PATENT DOCUMENTS

| | | | |
|---|---|---|---|
| EP | 1832250 A1 * | 9/2007 | |
| FR | 2616666 A1 * | 12/1988 | |
| FR | 2696636 A1 * | 4/1994 | |
| WO | WO 9113592 | 9/1991 | |
| WO | WO 9735524 A1 * | 10/1997 | |
| WO | WO 0016703 A1 * | 3/2000 | |

* cited by examiner

MEDICAL RETRIEVER

RELATED APPLICATIONS

This application is a continuation of International Application PCT/EP03/04164 filed 22 Apr. 2003 which is a continuation of German application serial number 10217757.0 filed 20 Apr. 2002, which are incorporated herein by reference.

The invention relates to a device for extracting a spiral helix from a blood vessel. The invention, furthermore, relates to a combination comprising such a device and a catheter.

For the treatment of vascular defects, for example aneurysms or arterial fistulae, embolization spirals are frequently used that are positioned at the implantation site with the aid of micro-catheters. In this connection, so-called "floating coils" are released close to the placement site and are carried by the blood stream towards the target position. Other forms of spirals are separated from the catheter when the ultimate target is reached. The placement techniques are very reliable but more often than not the necessity may still arise to extract or retrieve wrongly placed or washed away spiral. Nevertheless, known extraction devices fail when used in vessels that are so narrow that the stuck spiral can no longer be taken hold of by means of customary gripping devices.

From international patent application WO 91/13592 A1 a device having an electrode cable in the form of a spiral helix is known for the extraction of a cardiac pacemaker electrode grown into heart tissue with said device being provided with an anchoring part in the form of a slotted tubular segment attached to the distal end of the pull wire and having ends pointing towards the tube and being slightly pre-expanded outwardly. By drawing the pull wire the pre-expanded, slotted tubular segment is activated causing the tubular segment halves to be spread apart and thus enable their free ends to engage with the inner diameter of the spiral helix of the electrode cable.

For the known device it is necessary to provide different sizes of the anchoring part of the extraction device to suit the respective internal diameter of the electrode cable. Another drawback is encountered with the tubular segment halves that may fold over when used on too large an internal diameter in which case a safe anchoring effect can no longer be warranted. Moreover, this known extraction device is only reliably used with electrode cables forming multiple coils, particularly with quadruple-coil type electrodes. Using this device for the extraction of coils gone astray which usually have coiled themselves up and formed entanglements is not conceivable.

Spiral helixes having a length of several centimeters usually form into entanglements so that life-threatening occlusions may occur within the vascular system depending on the type of material the spirals are made of. In the event they are washed away entering the heart, brain or lungs complications may arise that may endanger the life of patients.

Proceeding from this state of the art the objective of the invention is to provide an extraction device or retriever capable of extracting spiral helixes of a variety of configurations involving singly or multiply coiled spirals. In particular, the invention shall make it possible to retrieve lost spirals from vessels of narrow lumen.

This objective is reached by providing a device for the extraction of a spiral helix from a blood vessel with said device having a guide wire which bends back on itself in its distal region where it forms into a loop structure with its free end pointing towards the catheter so that it can be hooked onto the spiral to be extracted.

The device according to the invention basically consists of a customary guide wire the distal end of which is bent back on itself by mechanical means so that it forms a hook-like structure. As a rule, the distal end which has been bent backwards has a length ranging between 1 and 3 cm, The guide wires to be employed are equivalent to those used in the micro-catheter technology, that is they have diameters between 0.1 and 0.5 mm. To improve the functionality of these guide wires they are expediently provided with a conventional hydrophilic coating.

It is essential for the guide wires applied in accordance with the invention to be highly flexible within their functional part so that they are capable of adjusting themselves to and follow the run of the vascular system in the human body without difficulty. Flexibility will promote and be conducive to the process of capturing and hooking onto a lost spiral helix which is to be extracted. Guide wires whose flexibility increases in distal direction are particularly expedient to the intended purpose. Characteristics of this nature will enable the free end of the guide wire to which the captured spiral is attached to wind or coil around the proximally situated portion of the guide wire.

In its most simple structure the anchoring part has a hook-like form which means the distal end of the guide wire is bent back on itself and is shaped like an arched structure (loop) with the end of the guide wire which has been bent back and is pointing towards the proximal side being able to move freely.

According to a preferred embodiment the loop created as a result of the distal end of the guide wire being bent back does not extend in the direction of the guide wire but, at least in its distal area, is slightly inclined in its plane relative to the run of the guide wire. It is particularly easy for this embodiment to be steered through vascular bends and ramifications. Preferably, also the distal end of the guide wire (the free end of the loop) is inclined or arranged at an angle relative to the run of the guide wire which is conducive to the capturing process.

In accordance with a preferred embodiment of the invention the free end of the guide wire has a corkscrew configuration resulting in an improved hooking performance further assisting the seizing of spiral helixes to be extracted. In line with another expedient embodiment the guide wire end bent back may at its end be provided with a thicker ball-shaped portion which as well makes the seizing process easier.

To secure or maintain the hook structure in position it may be expedient to locate the bent-back free end of the guide wire at the guide wire itself with the aid of a sleeve shown at 4a in FIG. 1a. In this case the loop-shaped structure into which the guide wire has been formed at its distal end is retained in position by the sleeve 4a. The sleeve 4a may consist of any material compatible with the body but, expediently, should be made of a metal which has radiopaque characteristics. According to another preferred embodiment of the invention the free end of the loop-shaped structure may be set free out of the sleeve.

In the interest of monitoring the extraction process it is especially expedient for the free end of the guide wire as well to be, at least partially, of radiopaque design. This may be brought about by using a radiopaque metal, for example platinum or gold, for the guide wire proper in this area or through the use of a radiopaque plastic coating such as for example by the incorporation of radiopaque metal dust into the plastic coating. Such measures are sufficiently known to persons averagely skilled in the art.

With the help of the device according to the invention spiral helixes lost or is wrongly placed in the vascular system may also be retrieved and retracted from narrow vessels. For this purpose the anchoring part of the retriever in accordance with the invention is positioned behind the spiral helix which is then captured by retracting the guide wire. Subsequently, by twisting the micro-guide wire the metal spiral is wound about the center (the axis) of the guide wire so that the highly flexible distal end of the folded-back portion wraps around the rotating axis of the guide wire and thus around the captured spiral.

During the extraction process the previously applied and determined wire turning direction must not be changed because the fastening thread may otherwise become uncoiled—causing the hook to open and the spiral to be released.

As a result of the radiopaque marking the complete capturing and extraction process can be monitored.

Moreover, the invention relates to a combination comprising the device according to the invention and a catheter, in particular a micro-catheter. As per a preferred embodiment of this combination the device in accordance with the invention is provided with a customary operating system in which the guide wire is connected to a handle sleeve in a manner so as to withstand torque and attached to a bushing secured within or onto the proximal end of the catheter.

Figure 2:
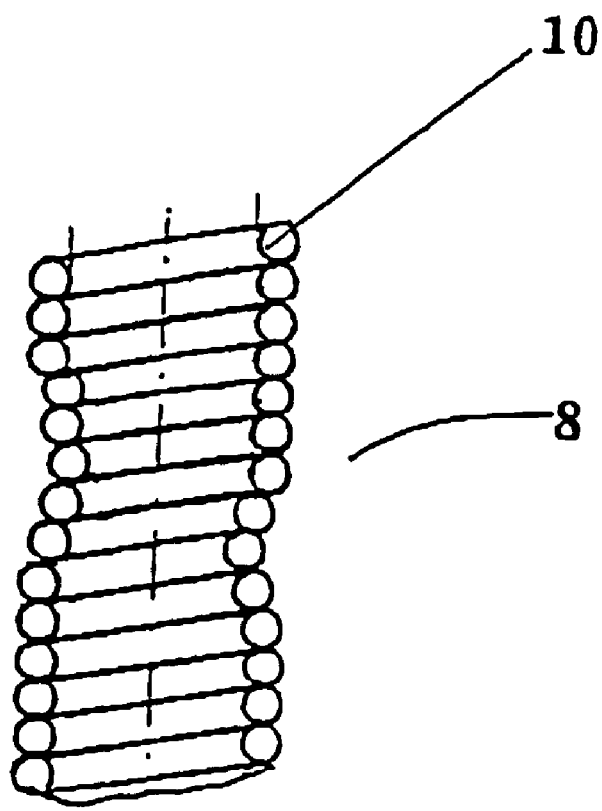

The invention is explained in more detail by way of the enclosed figures. The following figures are enlarged representations showing:

FIG. 1 an embodiment of the present invention in the form of the combination of a catheter with a device according to the invention for the extraction of spiral helixes;

FIG. 1a an embodiment of the present invention in which the free end of the guide wire has a corkscrew-like configuration;

FIG. 1b a side view of the embodiment illustrated in FIG. 1;

FIG. 2 a section of a customary spiral helix and

Figure 3:
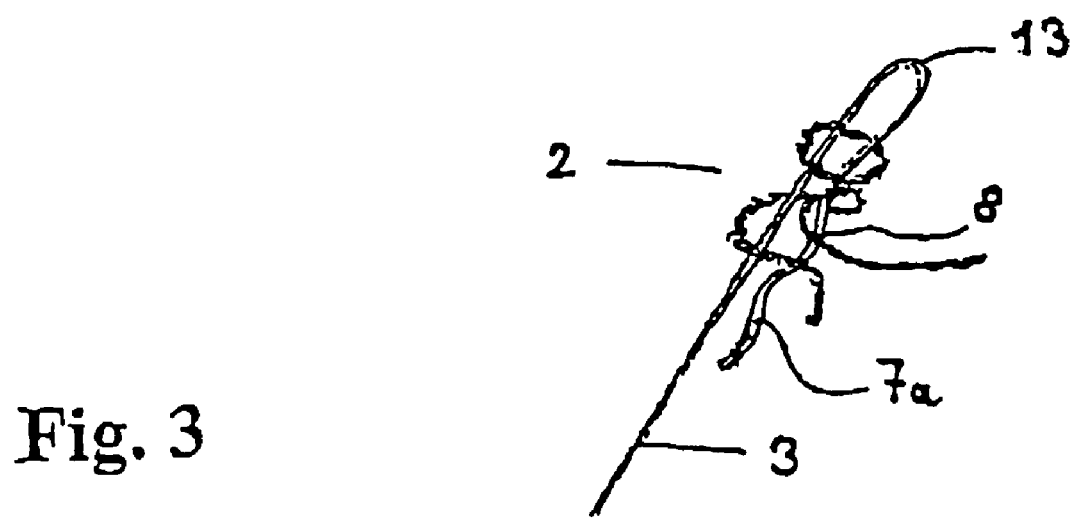

FIG. 3 a spiral helix captured by means of the retriever in accordance with the invention.

The retriever combination 1 illustrated in FIG. 1 comprises the guide wire 3 bent so as to form anchoring part 2, the catheter 5 as well as the operating system 6. The representation only serves for illustration purposes and is not true to scale. The guide wire 3 is passed through the catheter tube 5 and located within the operating system 6 attached to handle sleeve 17, said wire being rotatable by turning the handle sleeve 17 relative to the bushing 18.

The proximal end 19 of the catheter tube 5 has been illustrated on the side of bushing 18 opposite the one facing the handle sleeve 17.

For the purpose of forming the anchoring part, the guide wire 3 is bent back on itself at its distal end with the free end 7 pointing towards the distal end 11 of catheter 5. The loop structure 4 thus formed has a distal end 13 constituting the front end of the retriever being advanced through the respective blood vessel. The loop 4 of the anchoring part 2 is of slightly inclined arrangement relative to the axis of the guide wire body which makes it especially easy to maneuver the retriever 1 through the bends and ramifications of the blood vessel system.

FIG. 1a shows another preferred embodiment in which the free end of guide wire 3 has been shaped to form a corkscrew structure 7a arranged on the other side of loop 4. The loop-like configuration 4 is clearly seen in the figure and—apparent from the exaggerated arrangement—results distally in a blunt end of the anchoring part so that injuries to the vascular system are avoided. Otherwise, the guide wire 3 itself is made of a highly elastic material provided with hydrophilic coating as is usually employed for micro-guide wires which per se is conducive to the prevention of injuries.

FIG. 1b is a side view of the loop 4 illustrated in FIG. 1. As can be seen from the figure, the loop is inclined relative to the axis/the run of the guide wire 3 and, moreover, the free end 7 is of angled arrangement.

FIG. 2 shows a portion of a customary embolization spiral 8 as a cross section through the coils 10. Such embolization spirals 8 have effective diameters ranging between 0.1 and 0.5 mm and, more often than not, are several centimeters long so that internal entanglements are easily caused. Such entangled spiral helixes permit the anchoring part according to the invention to hook on, clear the entanglement and wind the thus captured spiral around the guide wire 3 in the area of the anchoring part 2 by performing a simple rotating movement. Capturing the spiral takes place primarily via the free end 7 functioning as a hook; winding the spiral up causes this hook to tighten so that the spiral helix remains captured.

FIG. 3 shows part of a spiral helix 8 captured by means of anchoring part 2 according to the invention with said spiral being caught up in the anchoring part and wound around anchoring part 2 as a result of the turning action of the guide wire 3. Anchoring part 2 in this example has not been provided with a safety sleeve which renders it particularly atraumatic and most expedient in the event coils have to be captured in vessel branches of very narrow lumen.

I claim:

1. A medical retrieving device for capturing and extraction of a spiral helix from a blood vessel with said device having a guide wire (3), having a proximal end, a distal region, and a free end, and which bends back on itself in its distal region where it consists of a loop structure (13) so that an anchoring part (2) in the form of a hook is created, with the free end (7) of the guide wire (3) pointing towards the proximal end of the guide wire (3) so that it can be hooked on the spiral helix (8) to be extracted, wherein the device is characterized in that the free end (7) of guide wire (3) has a corkscrew-like configuration pointing to the proximal end of the guide wire (3), and further characterized in that at least the distal region of the loop structure (13) is arranged at an angle relative to a run of the guide wire (3) which is conducive to the capturing process and further characterized in that the loop structure (13) forms a loop (4) having a plane formed by the loop, said plane being inclined relative to the run of the guide wire (3), for facilitating steering of the medical retrieving device through vascular bends.

2. The device of claim 1, characterized in that the guide wire (3) has been provided with a hydrophilic coating.

3. The device of claim 1, characterized in that the diameter of the guide wire (3) ranges between 0.1 and 0.5 mm at its free end (7).

4. The device of claim 1, 2, or 3 characterized in that the free end (7) is secured by means of a sleeve (4a) on the guide wire (3) thus causing a loop (13) to form.

5. The device of claim 4, characterized in that the sleeve (4a) is of radiopaque design.

6. The device of claim 1, 2, or 3 characterized in that the free end (7), at least partially, is of radiopaque design.

7. The device of claim 6, characterized in that the free end (7) of guide wire (3) has been provided with a radiopaque coating.

8. The device of claim 7, characterized in that metal dust is incorporated into the radiopaque coating.

9. The device of claim 1, 2, or 3 characterized in that the free end (7) of guide wire (3) is highly flexible so that it wraps around the guide wire (3) when the guide wire (3) is rotated.

10. The device of claim 1 in which the free end (7) of guide wire (3) is able to move freely relative to the run of the guidewire.

11. A combination comprising a device of claim 1 or 2, and a micro-catheter.

12. The combination of claim 11, characterized by an operating system (6) in which the guide wire (3) is connected to a handle sleeve (17) in a manner so as to withstand torque and attached to a bushing (18) secured within or onto the proximal end (19) or the catheter.

* * * * *